United States Patent
Dallmann

(10) Patent No.: US 8,690,952 B2
(45) Date of Patent: *Apr. 8, 2014

(54) SHOULDER PROSTHESIS

(75) Inventor: Frank Dallmann, Schmoelln (DE)

(73) Assignee: Mathys AG Bettlach, Bettlach (CH)

( * ) Notice: Subject to any disclaimer, the term of this patent is extended or adjusted under 35 U.S.C. 154(b) by 507 days.

This patent is subject to a terminal disclaimer.

(21) Appl. No.: 12/300,454

(22) PCT Filed: Apr. 25, 2007

(86) PCT No.: PCT/EP2007/003661
§ 371 (c)(1),
(2), (4) Date: Nov. 11, 2008

(87) PCT Pub. No.: WO2007/134691
PCT Pub. Date: Nov. 29, 2007

(65) Prior Publication Data
US 2009/0164021 A1 Jun. 25, 2009

(30) Foreign Application Priority Data

May 22, 2006 (DE) .......................... 10 2006 023 957
Sep. 5, 2006 (DE) .......................... 10 2006 041 551

(51) Int. Cl.
*A61F 2/40* (2006.01)
(52) U.S. Cl.
USPC .................................... 623/19.13; 612/19.12
(58) Field of Classification Search
None
See application file for complete search history.

(56) References Cited

U.S. PATENT DOCUMENTS

| 4,206,517 A | 6/1980 | Pappas et al. | |
|---|---|---|---|
| 4,964,865 A * | 10/1990 | Burkhead et al. | 623/19.11 |
| 5,108,447 A * | 4/1992 | Zeiler et al. | 623/22.14 |
| 5,593,448 A * | 1/1997 | Dong | 623/19.11 |
| 6,695,845 B2 * | 2/2004 | Dixon et al. | 606/70 |
| 6,953,478 B2 * | 10/2005 | Bouttens et al. | 623/19.11 |
| 2005/0209700 A1 * | 9/2005 | Rockwood et al. | 623/19.12 |
| 2005/0261775 A1 * | 11/2005 | Baum et al. | 623/19.12 |
| 2005/0278032 A1 | 12/2005 | Tornier et al. | |
| 2007/0244563 A1 * | 10/2007 | Roche et al. | 623/19.12 |
| 2008/0228281 A1 * | 9/2008 | Forrer et al. | 623/19.12 |
| 2009/0149961 A1 * | 6/2009 | Dallmann | 623/19.11 |

FOREIGN PATENT DOCUMENTS

| AU | 2004216605 | 4/2005 |
|---|---|---|
| EP | 1 064 890 | 1/2001 |
| EP | 1 520 561 | 4/2005 |
| EP | 1 607 070 | 12/2005 |
| FR | 2 704 747 | 11/1994 |

OTHER PUBLICATIONS

Roche et al. U.S. publication No. 2007/0244563, clean drawings submitted to USPTO Mar. 23, 2007.*
International Search Report for PCT/EP2007/003661 dated Aug. 9, 2007.

* cited by examiner

*Primary Examiner* — Marcia Hoffman
(74) *Attorney, Agent, or Firm* — Marshall, Gerstein & Borun LLP

(57) ABSTRACT

A shoulder prosthesis comprising a socket and a condyle that cooperates with the socket. The condyle also cooperates with a base plate facing the scapula similar to a clamping connection. The condyle is plugged onto the base plate by means of a receptacle that is embodied on the condyle. The base plate can be anchored to the glenoid fossa of the scapula with the aid of two peg-type protrusions.

14 Claims, 9 Drawing Sheets

SHOULDER PROSTHESIS

BACKGROUND OF THE INVENTION

Field of the Invention

The present invention relates to a shoulder prosthesis having a condyle and an articulation socket which co-operates therewith. In particular, the present invention relates to a so-called inverse shoulder prosthesis.

Shoulder prostheses of the generic type are generally constructed in such a manner that an articulation socket which co-operates with a condyle is secured to an upper arm bone, the so-called humerus, which co-operates with a condyle which is secured in an anatomical glenoid cavity (Cavitas Glenoidalis) of a shoulder blade (scapula). In contrast to the anatomical shoulder joint, in which the ball-like humerus head of the upper arm bone forms a ball and socket joint with the glenoid cavity of the shoulder blade, the arrangement between the condyle and the articulation socket is therefore transposed in this shoulder prosthesis and accordingly constitutes an inverse shoulder joint.

In these inverse shoulder prostheses, there is the problem that, when the upper arm is moved towards the upper body (adduction), the articulation socket which is fixed to the humerus slides along the condyle with, if the upper arm is adducted to a very high degree, a portion of the articulation socket protruding beyond an edge of the condyle in such a manner that it abuts against a lower edge of the Cavitas Glenoidalis of the shoulder blade. This may first of all cause occurrences of wear and damage to the bone material. However, a far more significant problem is that there is also the risk that the edge of the articulation socket will at a later stage collide with screws which are used to anchor the condyle in the shoulder blade. This may ultimately lead to these screws becoming damaged or even broken so that secure anchoring of the condyle in the shoulder blade is no longer ensured.

In order to avoid this effect of so-called inferior notching, attempts have already been made to arrange the condyle in an offset manner on the Cavitas Glenoidalis in the direction towards a lower corner of the shoulder blade, the so-called Angulus Inferior. In this regard, EP 1 607 070 A1, for example, discloses a shoulder prosthesis in which the condyle is fitted to a base plate which is in turn anchored to the shoulder blade by means of a pin-like protrusion. The protrusion in this instance is arranged on the base plate centrally relative to the center axis of the base plate at the shoulder blade side, the condyle having, for the base plate, a receptacle which is orientated eccentrically relative to the center axis thereof. Although it is possible to enlarge the movement clearance in which a collision of the articulation socket with the bone material is prevented owing to the resultant offset arrangement of the condyle, the problem of inferior notching has not been completely overcome thereby. In this solution too, if additional screws are used to anchor the base plate to the shoulder blade in addition to the pin-like protrusion, there is the danger that they will become damaged over time.

Another problem with the shoulder prosthesis described in EP 1 607 070 A1 mentioned above is that a reliable arrangement of the condyle with the desired orientation can be achieved only with difficulty on the shoulder blade. The conventional procedure during the operation involves a doctor first forming in the shoulder blade a hole which corresponds to the pin-like protrusion and into which the base plate is then introduced and anchored with the pin. It is not possible in this instance for the doctor to determine a preferred rotational orientation of the base plate, for which reason there is a danger that the base plate will be arranged on the shoulder blade with poor orientation. Ultimately, this leads to the shoulder prosthesis not being able to be inserted with the desired level of precision.

GENERAL DESCRIPTION OF THE INVENTION

Accordingly, the problem addressed by the present invention is to avoid the disadvantages of the previously known shoulder prosthesis. In particular, a new type of shoulder prosthesis is intended to be provided which has a particularly good and reliable implantation technique and force transmission at the anchoring interfaces with the anatomical shoulder blade in order to enable increased service-life of the material and more precise and improved reliability in terms of anchoring.

The problem is solved by a shoulder prosthesis having an articulation socket and a condyle which co-operates therewith and which co-operates with a scapula-side base plate in the manner of a clamping connection, the condyle being fitted to the base plate by means of a receptacle which is formed thereon and which can be anchored to the Cavitas Glenoidalis of the scapula by means of two pin-like protrusions which are arranged on the base plate.

In principle, the present invention is based on the notion of anchoring the base plate, which is provided to secure the condyle to the shoulder blade, to the Cavitas Glenoidalis of the scapula using two pin-like protrusions. In contrast to the solution known from EP 1 607 070 A1, in which the base plate is secured using only one protrusion, the solution according to the invention affords clear advantages with regard to the procedure for securing the shoulder prosthesis and with respect to the anchoring which can be achieved in this case. As will be explained in greater detail below, the use of two protrusions according to the invention enables damage caused to additional anchoring elements by the inferior notching described above to be prevented. Furthermore, the use of the two projections also allows anchoring elements which are additionally used to be arranged and orientated in such a manner that they can engage in an optimum manner in the bone material of the shoulder blade. This therefore again allows further improved anchoring of the shoulder prosthesis to the shoulder blade. Finally, by means of the two protrusions, together with the pilot holes which are defined beforehand and which are formed for the two protrusions, a correct rotational orientation of the base plate on the shoulder blade is ensured, for which reason it is far simpler for a doctor to secure the shoulder prosthesis correctly in the desired manner when fitting the shoulder prosthesis.

According to the invention, a shoulder prosthesis is therefore proposed with an articulation socket and a condyle which co-operates therewith, the condyle co-operating with a scapula-side base plate in the manner of a clamping connection, and the condyle further being fitted to the base plate by means of a receptacle which is formed therein and which can be anchored to the Cavitas Glenoidalis of the scapula by means of two pin-like protrusions which are arranged on the base plate.

Preferred embodiments of the invention relate in particular to the configuration of the base plate.

For instance, firstly in accordance with a particularly preferred configuration of the present invention, there is provision for the base plate to be able to be secured on the Cavitas Glenoidalis an offset towards an Angulus Inferior of the scapula. To this end, the base plate has in particular a dome-like base face which is provided for abutment against the Cavitas Glenoidalis of the Scapula, the center of the dome-like shape being arranged eccentrically relative to the center axis of the base plate. The center of this dome-like shape is preferably arranged on a straight connecting line between the two protrusions and in particular displaced in the opposite direction to the Angulus Inferior of the scapula.

The receptacle of the condyle for the base plate is in contrast preferably formed centrally relative to the center axis thereof. Together with the above-mentioned feature of the eccentric configuration of the base face of the base plate, this enables the desired offset arrangement of the condyle on the shoulder blade to be achieved in a simple manner. The particular nature of this consists in the fact that the contact face of the Cavitas Glenoidalis can be constructed in a simple manner so as to be shaped in the manner of a spherical portion in order to fit together with the dome-like base face. This also contributes to simplified assembly of the condyle on the shoulder blade, since the required processing of the Cavitas Glenoidalis can be carried out by the surgeon in a simple manner.

As already mentioned above, the use of the two protrusions in particular advantageously allows additional anchoring elements to be used to secure the base plate to the shoulder blade. According to another preferred embodiment, there is accordingly provision for the base plate to be able to be additionally anchored to the Cavitas Glenoidalis by means of anchoring elements which can be received in sleeves provided on the base plate. At least one of the two sleeves is arranged to the side of the straight connecting line between the two protrusions. A sleeve for receiving an anchoring element is preferably arranged at both sides of the straight connecting line between the two protrusions. A particular advantage of this configuration is that, owing to the use of the two protrusions, the two anchoring elements, which are preferably screws, can be offset further towards the center of the base plate. This ensures that the anchoring elements can penetrate reliably and securely into the bone material of the shoulder blade. In this manner, the securing of the shoulder prosthesis is therefore again further optimized.

The sleeves may have, at a side of the base plate facing away from the scapula, recesses for heads which are provided on the anchoring elements. At least one of the sleeves may be constructed in such a manner that the corresponding anchoring element is spread apart in the manner of a finger of an open hand after the final assembly of the shoulder prosthesis, whereby the anchoring of the prosthesis in the shoulder blade is again improved. This sleeve for angularly stable support of an anchoring element preferably has a screw thread for forming a screw connection with the associated anchoring element. The additional sleeves are in contrast preferably constructed in such a manner that the associated anchoring elements are orientated substantially parallel with the protrusions, but with a slight clearance being provided in the alignment of these anchoring elements in order to facilitate assembly.

A receptacle side face on the condyle and an outer face of the base plate that co-operates therewith are preferably constructed so as to be circular in order to form the clamping connection. In order to allow the condyle to be arranged on the base plate in a manner which is secure in terms of rotation, the condyle preferably has, at a side facing away from the Angulus Inferior of the scapula, a groove which co-operates with a tongue or protuberance which is formed on the base plate. There may in particular also be provision for an additional sleeve for receiving an additional anchoring element to be provided in the region of this tongue or protuberance on the base plate. The receptacle on the condyle is preferably sized in such a manner that the scapula-side base face of the base plate and a scapula-side edge face of the condyle adjoin each other in a substantially flush manner.

Seen as a whole, owing to these configurations a shoulder prosthesis is obtained which can be arranged and anchored on the shoulder blade in a simple but particularly reliable manner. Furthermore, damage to the elements required for anchoring on the shoulder blade can be eliminated to the greatest possible extent.

BRIEF DESCRIPTION OF THE DRAWINGS

The invention is to be explained in greater detail below with reference to the appended drawings, in which.

DETAILED DESCRIPTION

Figure 1:
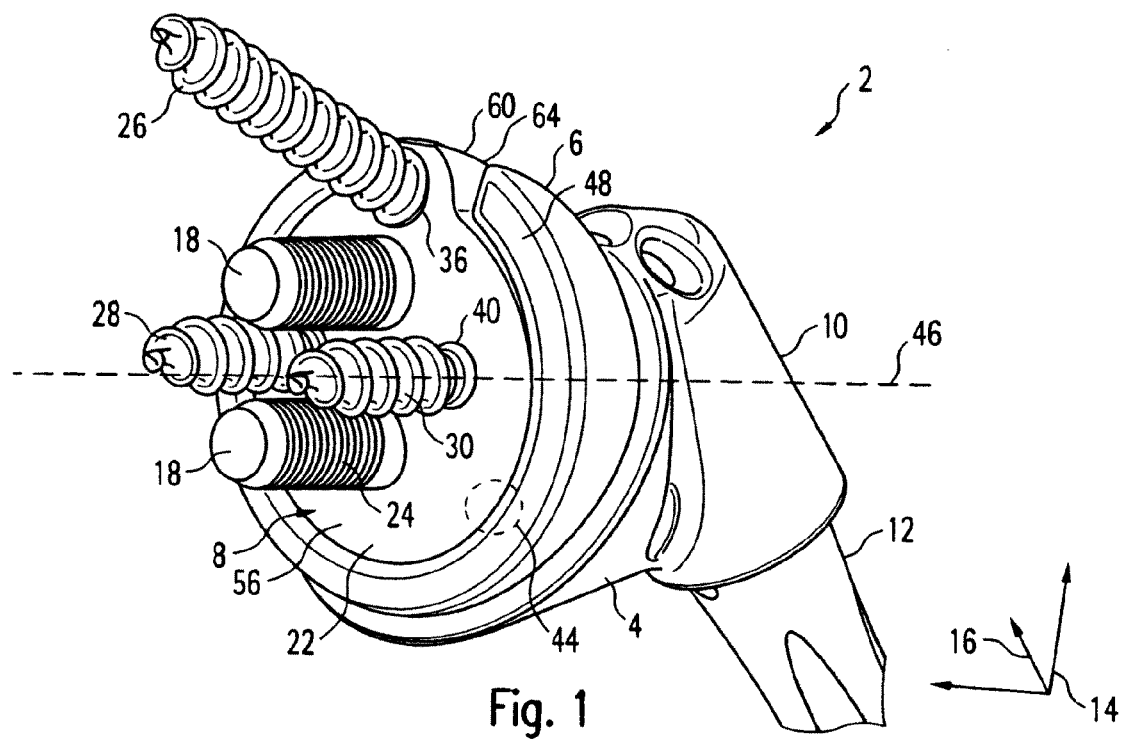
FIG. 1 is a first view of a shoulder prosthesis according to the invention having an articulation socket and a condyle and a base plate which is connected to the condyle with the corresponding anchoring elements.
Figure 2:
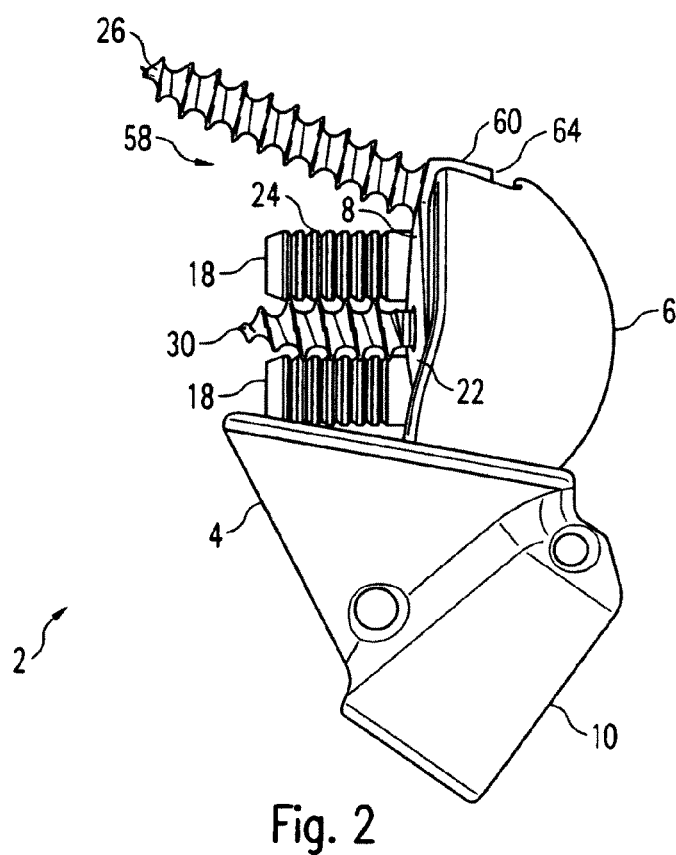
FIG. 2 is another view of the shoulder prosthesis according to the invention.
Figure 3:
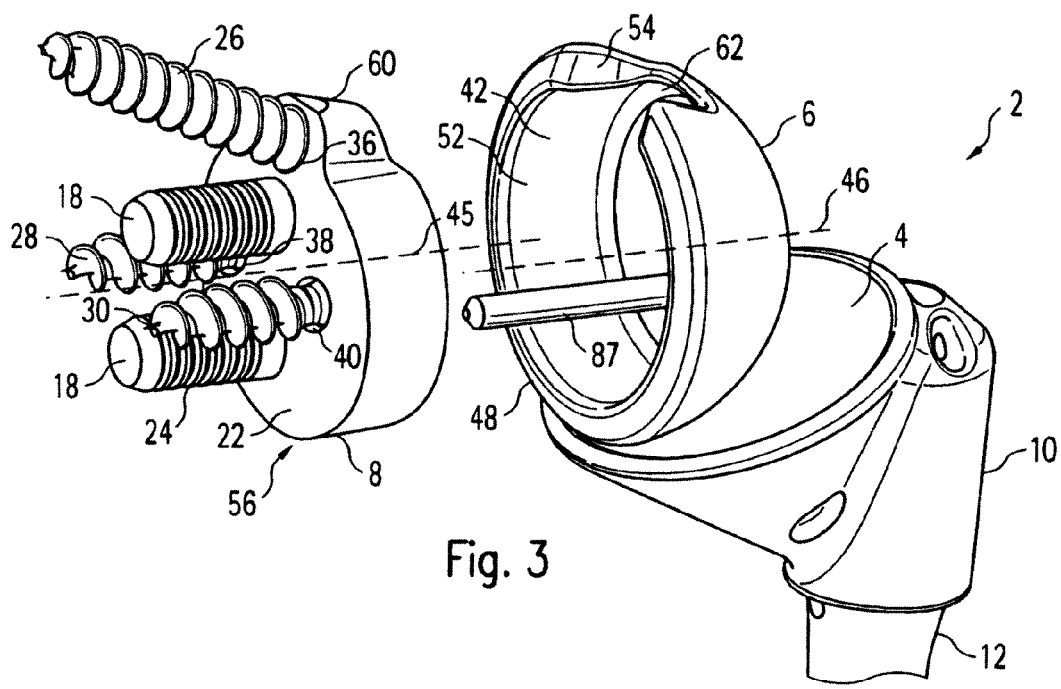
FIGS. 3 and 4 are two exploded views of the shoulder prosthesis according to the invention.
Figure 4:
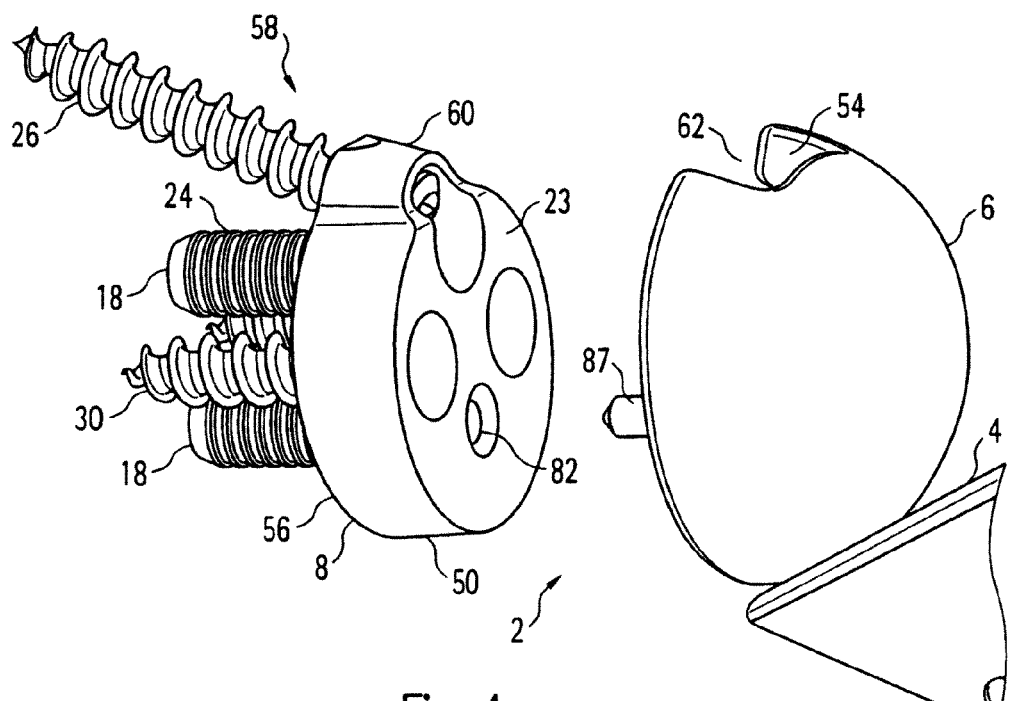

FIGS. 1 to 4 illustrate different views of the shoulder prosthesis according to the invention, generally designated 2. FIGS. 1 and 2 show the shoulder prosthesis 2 in the joined-together state, whilst FIGS. 3 and 4 are exploded views.

Significant integral components of the shoulder prosthesis 2 are an articulation socket 4 and a condyle 6 which co-operate in the manner of a ball and socket joint. The condyle 6 is fitted to a base plate 8. The articulation socket 4 is in turn connected, by means of a coupling piece 10, to a rod 12 which is recessed in the upper arm (humerus) by means of a humerus head which is not illustrated in FIGS. 1 to 4. The articulation socket 4 is arranged so as to be able to be pivoted in and counter to the directions indicated with the directional arrows 14 and 16 on the surface of the condyle 6, the so-called glenosphere. FIG. 1 shows the articulation socket 4 in a position in which the upper arm is adducted, but not adducted to such an extent that there would be any risk of damage to the bone material.

In order to anchor the shoulder prosthesis 2 according to the invention to a shoulder blade not illustrated in FIGS. 1 to 4, the so-called scapula, the base plate 8 has various elements which are introduced into the corresponding bone material of the shoulder blade.

These are firstly two pin-like protrusions 18 which are integrally formed with the base plate 8 and which are arranged substantially at right-angles to the base face 22 of the base plate 8. These pins 18 are constructed in the manner of a peg and have ribs 24 on their periphery. When assembling the shoulder prosthesis 2 on the shoulder blade, these pins 18 are recessed into openings which are formed during an operation and clamped by means of press-fitting.

Three screws 26, 28 and 30 constitute additional anchoring elements which are received in sleeves 36, 38 and 40 formed on the base plate 8. After the base plate 8 has been anchored using the two protrusions 18, the anchoring screws are screwed into the bone material of the shoulder blade in order to provide additional anchoring. They are guided on the base plate 8 in such a manner that the screw 26 is splayed slightly towards the upper side and the two additional screws 28 and 30 are orientated substantially parallel to the protrusions 18. These two screws 28 and 30 are primarily used to screw the base plate 8 securely to the shoulder blade initially. Subsequently, the screw 26, which is guided in an angularly stable manner, is introduced and the base plate 8 is secured to the bone, whereby particularly reliable anchoring of the base plate 8 and consequently the entire prosthesis 2 to the shoulder blade is brought about.

The condyle 6 comprises, for assembly with the base plate 8, a receptacle 42 (see FIG. 3) whose size for forming a clamping connection 44 between the condyle 6 and the base plate 8. The receptacle 42 is formed on the condyle centrally relative to the center axis 46 of the condyle 6. In order to form the clamping connection 44 between the condyle 6 and the base plate 8, an outer face 50 of the base plate 8 accordingly co-operates with a receptacle side face 52. The outer face 50 and the receptacle side face 52 are constructed so as to be circular in such a manner that a condyle wall 54 delimited by the edge face 48 has a consistent wall thickness in the region of the edge face 48 of the glenosphere. This is the consequence of the central receptacle for the base plate 8 and results in particularly uniform force transmission being ensured between the base plate 8 and the condyle 6. In this context, it should be noted that the connection between the base plate 8 and condyle 6 could also be produced in another manner by means of elements which co-operate in a positive-locking and/or non-positive-locking manner. Another example of this will be explained below. In order to produce the two elements, it is possible to use all the materials which are conventional in prosthetics, it also being completely possible to use a combination of elements of different materials.

As will be explained in greater detail below, the base face 22 of the base plate 8 has a slight dome-like shape, the center of this dome-like shape being offset relative to the center axis 45 of the base plate 8 and consequently also relative to the center axis 46 of the condyle. This affords particular advantages with respect to the assembly of the shoulder prosthesis 2 on the shoulder blade, which will also be explained in greater detail below.

It should further be noted that the receptacle 42 of the condyle 6 is sized in such a manner that the base plate 8 almost completely disappears in the receptacle 42 when the condyle 6 is fitted to the base plate 8. In particular, the edge face 48 of the condyle 6 adjoins the base face 22 of the base plate 8 in a practically flush manner.

In order to prevent as far as possible the bone material of the shoulder blade from becoming damaged when the arm is adducted to a high degree, the base plate 8 is intended to be fixed in an offset manner on the Cavitas Glenoidalis (not illustrated in FIGS. 1 to 4) counter to the direction of the arrow 14. This means that the base plate 8 having a lower portion 56 cannot be supported on the Cavitas Glenoidalis with the base face 22. To this end, it is desirable to increase the anchoring stability of the base plate 8, which is achieved by the sleeve 36 for receiving one of the anchoring screws 26 being formed in an upper portion 58 of the base plate 8. In order to form this sleeve 36 on the base plate on the upper portion 58 of the base plate in a manner which is secure in terms of detachment, the base plate has a protuberance or a tongue 60 which first provides the necessary space for the sleeve 36. Furthermore, this tongue 60 co-operates with a groove 62 which is provided on the condyle, in order to form a tongue-and-groove connection 64, which allows the condyle 6 to be fitted to the base plate 8 in a correct manner. Further, by means of this tongue-and-groove connection 64, twisting of the condyle 6 on the base plate 8 owing to forces acting radially on the condyle 6 is also prevented.

Another element that serves to fit the condyle 6 to the base plate 8 in the correct position is a centering pin 87 which protrudes from the inner side of the condyle 6 and engages in an opening 82 of the base plate 8. This opening 82 on the base plate 8 extends into the lower protrusion 18 so that sufficient length is provided to receive the centering pin 87. These are optional auxiliary means which facilitate the fitting of the condyle 6 to the base plate 8 which is secured to the bone.

Optionally, it would also be possible to dispense with these auxiliary means and it would also be conceivable to use alternative auxiliary means. One possible variant is illustrated by way of example in FIGS. 17 to 19.

Figure 5:
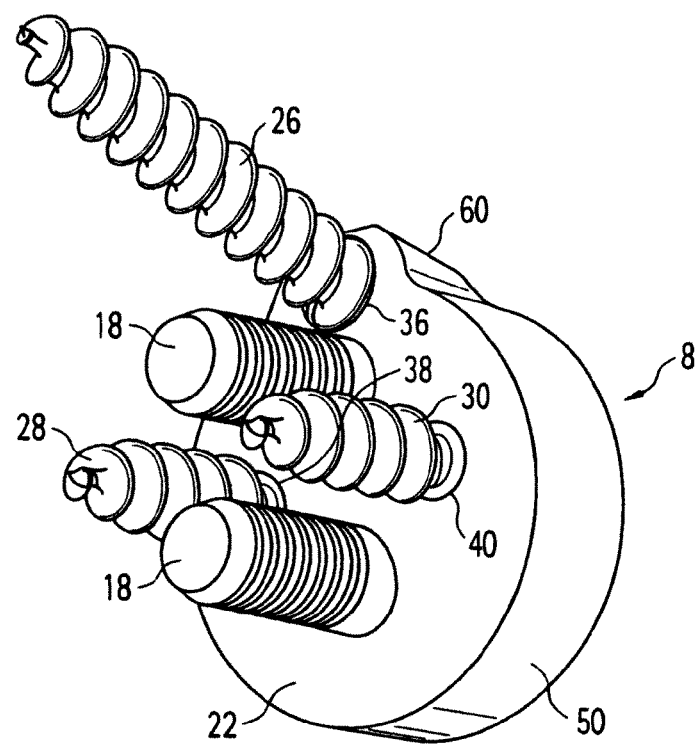
FIG. 5 is a view of the base plate with the two protrusions and the anchoring elements.
Figure 6:
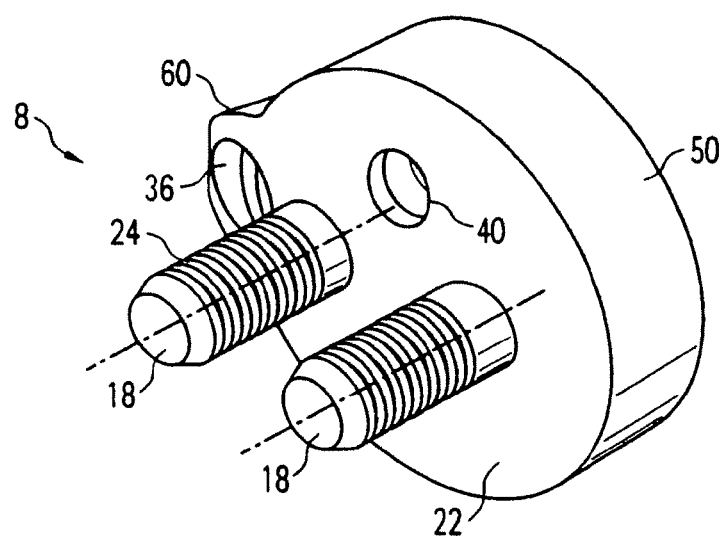
FIG. 6 is a view of the base plate without the anchoring elements.

FIG. 5 is a plan view of the base plate 8 in a state in which the anchoring screws 26, 28, 30 have also been introduced into the corresponding sleeves 36, 38, 40. The corresponding openings for introducing the screws 26, 28, can be seen in the exploded illustration of FIG. 4, in which the rear side 23 of the base plate 8 is shown. In addition to the three openings for the anchoring screws 26, 28, 30, the opening 82 for receiving the centering pin 87 is also shown.

With reference to FIGS. 6 to 9, the structure of the base plate 8 is to be described in greater detail below. It is particularly significant for the base face 22 of the base plate 8 to have the dome-like shape mentioned above. Furthermore, it should be emphasized in this context that the center 47 of the dome-like shape does not coincide with the geometric center or the center axis 45 of the substantially circular base plate 8. Instead, the center 47 of the dome-like shape is displaced by a distance L slightly in the direction towards the sleeve 36 for the upper anchoring screw 26. In this direction therefore the base face 22 of the base plate 8 has a degree of eccentricity. The center 47 of the dome-like shape is located on the straight connecting line 49 between the two protrusions 18 or on the axis of symmetry 51 which extends through the protrusions 18 and the tongue 60, as can be seen, on the one hand, from the illustration of FIG. 7 and, on the other hand, from the sectioned illustration of FIG. 9.

Figure 7:
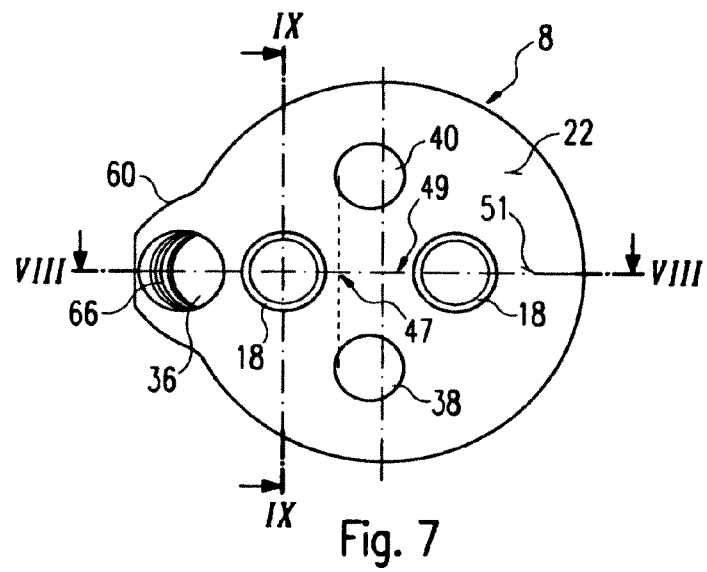
FIG. 7 is a plan view of the base face of the base plate.
Figure 8:
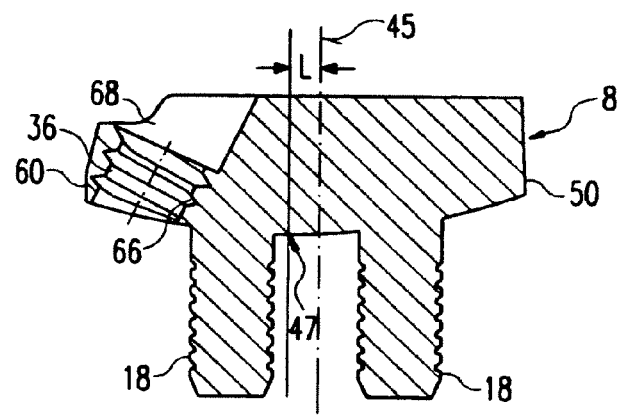
FIGS. 8 and 9 are sections through the illustration of the base plate according to FIG. 7.
Figure 9:
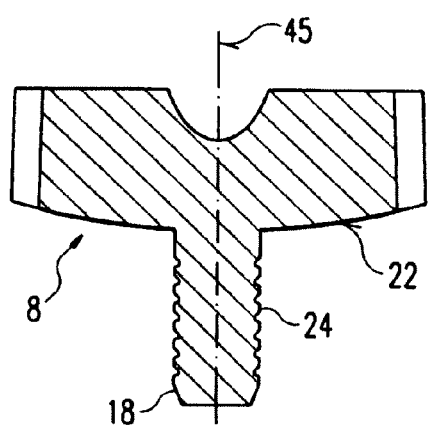

It can also be seen from the illustration of FIG. 7 that the sleeves 38 and 40 for the two additional anchoring screws 28 and 30 are arranged symmetrically relative to the axis of symmetry 51. In particular, the sleeves 38, 40 are located at both sides of the axis of symmetry 51 in the region between the two protrusions 18, respectively. Since neither of the two protrusions 18 is formed directly in the center of the base plate 8, it is accordingly possible to move the receiving sleeves 38, 40 closer to the axis of symmetry 51 which—as will be explained in greater detail below—affords particular advantages when anchoring the base plate 8 to the bone material of the shoulder blade.

It should further be emphasized that the sleeve 36 which, as mentioned above, is provided for angularly stable arrangement of the screw 26, has a screw thread 66. Using this thread 66, the screw 26, which is provided to secure the base plate 8 to the bone, can co-operate with the sleeve 36 by means of a screw connection. To this end, the sleeve 36 is further provided with a recess 68 for receiving the corresponding screw head.

The two additional sleeves 38, 40 are, however, constructed differently from the sleeve 36 since they are provided for retaining the screws 28 and 30, which perform a different function. These screws 28 and 30 are primarily used first to screw the base plate 8 securely to the shoulder blade before the splayed connection is brought about using the screw 26. The sleeves 38 and 40 are therefore orientated substantially parallel with the protrusions 18, have no threads and are further formed in the manner of a spherical portion at the upper region thereof. If screws with a spherical head are used as anchoring elements, they can be pivoted within a small angular range. This slight clearance allows the screws to be introduced into the shoulder blade in a more simple manner, thereby facilitating the assembly of the prosthesis.

This configuration of the sleeves 38 and 40 can in particular also be seen in FIGS. 10 to 13, which illustrate the co-operation of the base plate 8 with the condyle 6 and which are to be explained below.

Figure 13:
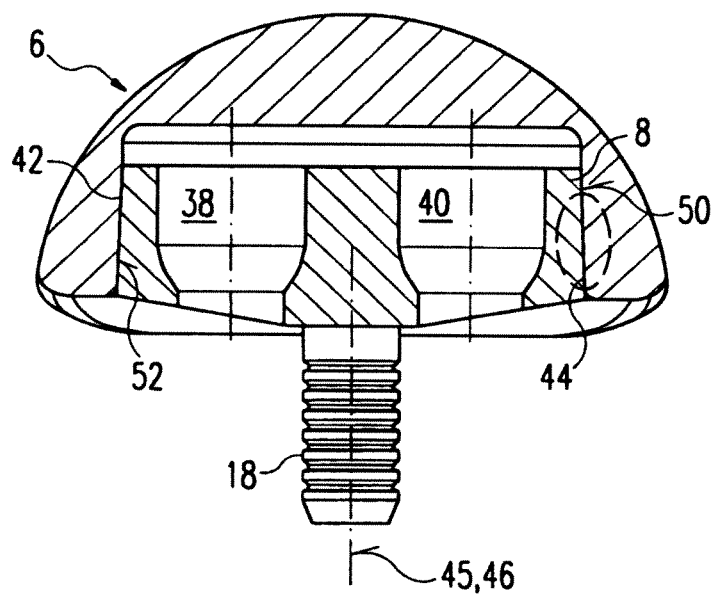

The condyle accordingly comprises the receptacle 42 which—as can be seen in particular from the illustration of FIG. 13—is formed on the condyle centrally relative to the center axis 46 thereof. With the exception of the tongue-and-groove connection 64, the peripheral wall of the condyle 6 accordingly has a uniform thickness, whereby particularly secure retention of the condyle 6 on the base plate 8 is enabled. The clamping connection 44 between the receptacle side face 52 of the condyle 6 and the outer face 50 of the base plate 8 contributes to this when the condyle 6 is fitted to the base plate 8.

In particular from the illustration in FIG. 12 it is possible again to see the eccentric configuration of the base face 22 in the base plate 8. It can clearly be seen that the center 47 of the protruding base face 22 is displaced slightly relative to the center axis 45 of the base plate 8 in the longitudinal direction towards the tongue-and-groove connection 64. However, a lateral deviation relative to the axis of symmetry is not present according to the illustration of FIG. 13, that is to say, the center of the dome-like shape coincides in this direction with the center axes 45 and 46 of the base plate 8 and the condyle 6.

Figure 12:
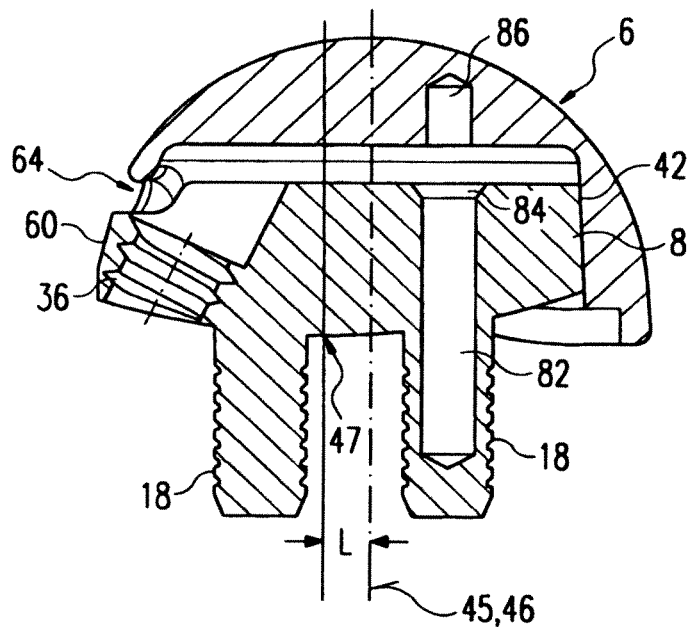
FIGS. 12 and 13 are two sections through the illustration according to FIG. 11.

From the illustration of FIG. 12, it is further possible to see the bore 82 of the base plate 8, which bore has an open end 84 at the condyle-side and extends at the scapula-side into the corresponding protrusion 18. In a continuation of this bore 82, a corresponding recess 86 is also formed in the condyle 6 and serves to receive the centering pin 87 illustrated in FIGS. 1 to 4, for centering the condyle 6 when it is fitted to the base plate 8. Together with the tongue-and-groove connection 64, an arrangement of the condyle 6 on the base plate 8 is thereby enabled which is secure in terms of rotation and the fitting of the condyle 6 to the pre-assembled base plate 8 is facilitated.

Figure 10:
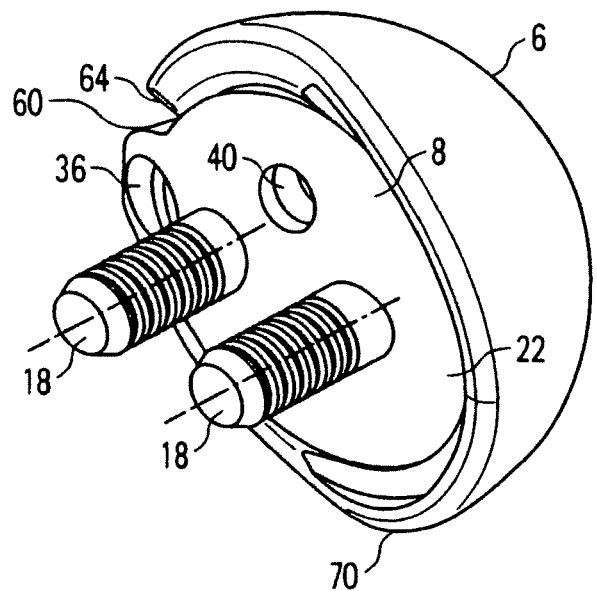
FIG. 10 is a view of the condyle connected to the base plate.
Figure 11:
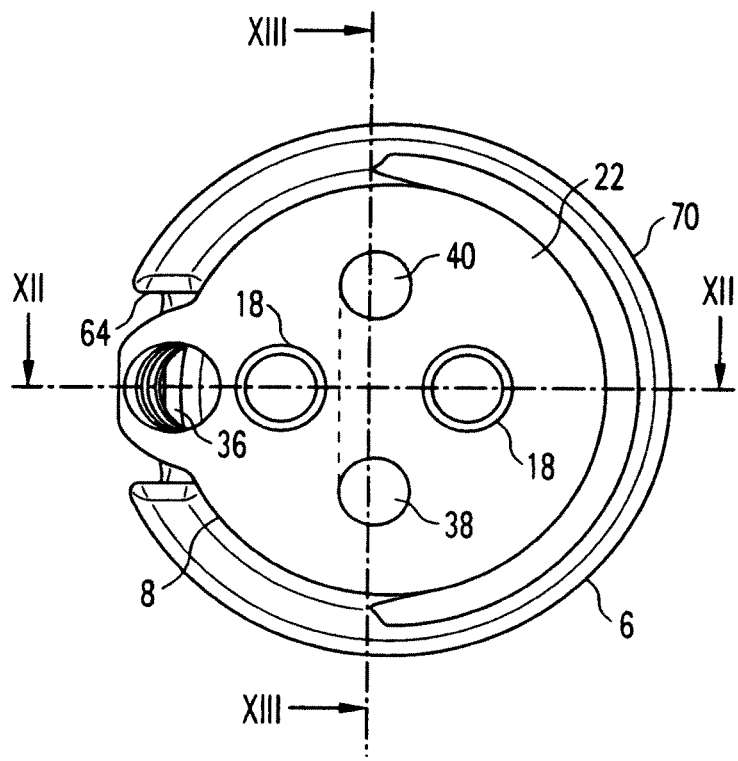
FIG. 11 is a plan view of the combination comprising the base plate and condyle.

Another specific feature which can be seen in particular from FIGS. 10 to 12 is that the outer face of the condyle 6 is pulled slightly in a downward direction in a region opposite the tongue-and-groove connection 64. This continuation of the outer face in the form of a lip 70, when the upper arm is adducted, results in an additional or extended guide being provided for the articulation socket 4. Another advantage of this configuration consists in that the contact face between the surface of the condyle 6 and the articulation socket 4 is increased when the arm is abducted so that ultimately a more uniform transmission of force can occur. In particular, the occurrence of punctual or linear contacts, which would lead to increased wear of the material, is reduced. In this context, it should also be mentioned that the condyle 6 forms a closed surface over its entire outer side. In particular, there are no openings or the like, which could potentially lead to punctual or linear contacts with the articulation socket 4, which affords clear advantages with respect to any potential wear of the material.

Figure 14:
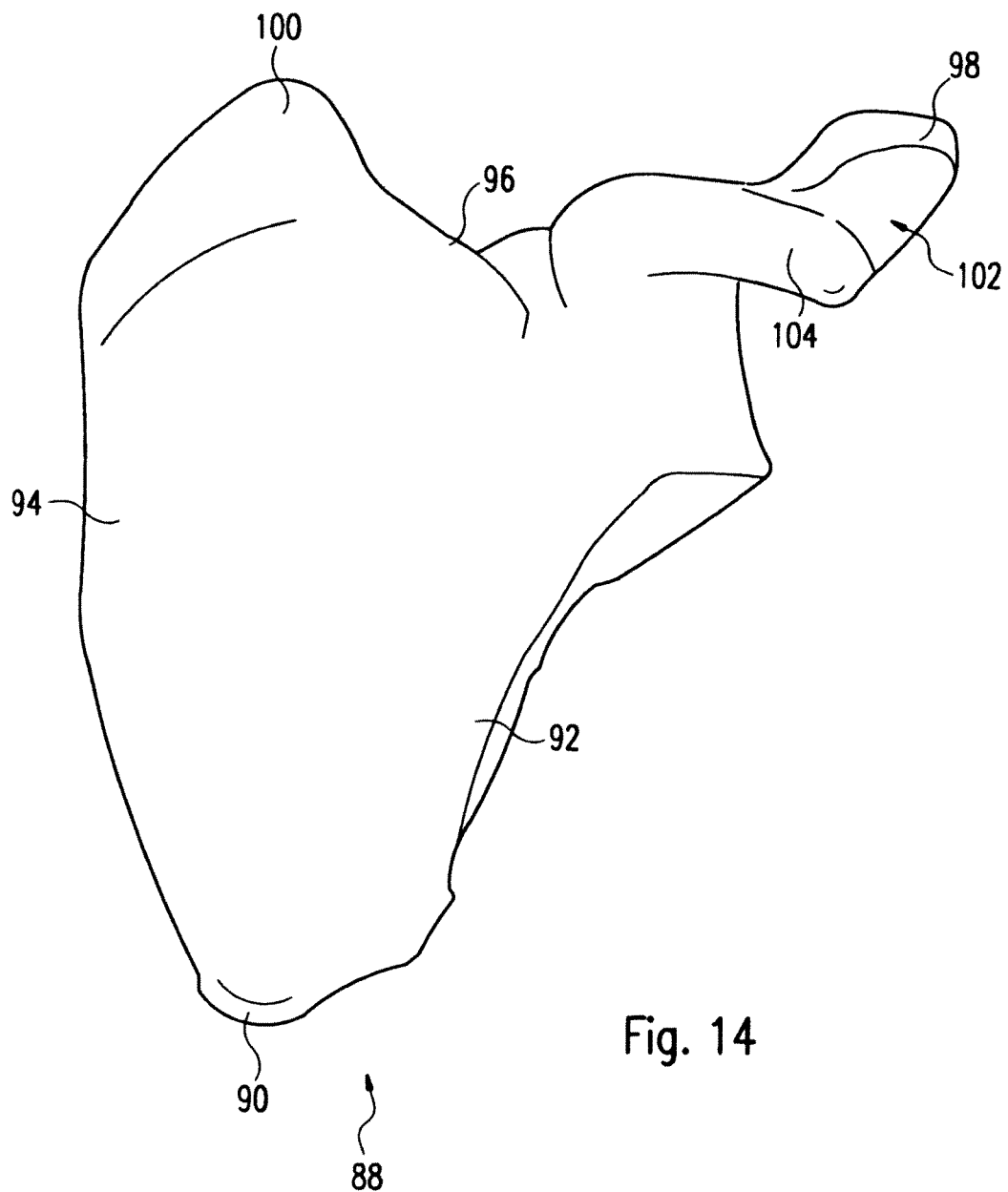
FIG. 14 is a view of an anatomical scapula (shoulder blade)

FIG. 14 is a plan view of an anatomical scapula 88, the shoulder blade, whose basic shape is that of a triangle. The lower corner of the triangle is referred to as the Angulus Inferior 90, which a right-hand edge "Margo Lateralis 92" and a left-hand edge "Margo Medialis 94" adjoin. The Margo Lateralis 92 and the Margo Medialis 94 delimit the upper edge "Margo Superior 96" at a right-hand corner "Angulus Lateralis 98" and at a left-hand corner "Angulus Superior 100". At the Angulus Lateralis 98, an anatomical articulation socket "Cavitas Glenoidalis 102" is positioned and has a coracoid process "Processus Coracoideus 104" which is curved forwards and outwards.

Figure 15:
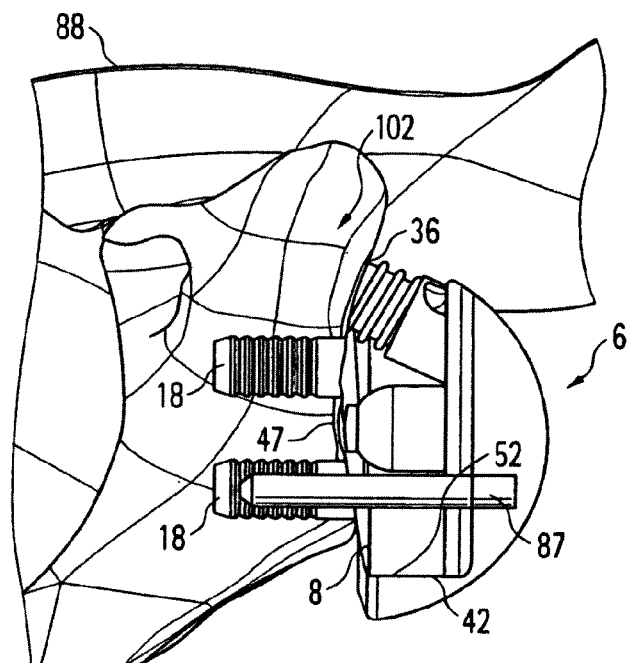
FIG. 15 is a sectioned view of the condyle which is secured to the scapula.
Figure 16:
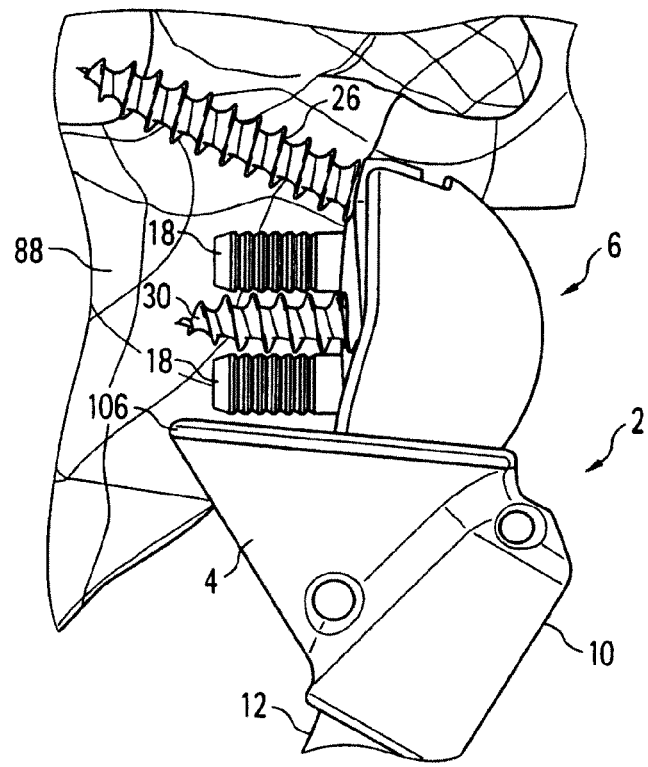
FIG. 16 is another sectioned view of the shoulder prosthesis according to the invention mounted on the shoulder blade.

FIGS. 15 and 16 respectively illustrate the condyle 6 secured to the shoulder blade using the base plate 8, and the shoulder prosthesis 2 completely secured to the shoulder joint. The articulation socket 4 which is secured to the rod 12 by means of the coupling piece 10 is fixed to the upper arm bone (humerus) which is not illustrated. The base plate 8 is in turn anchored to the Cavitas Glenoidalis 102 of the scapula 88 with the protrusions 18 and the anchoring screws 26, 28 and 30. The condyle 6 is fitted to the base plate 8 by means of the receptacle 42. The receptacle 42 is formed on the condyle centrally around the center axis 46 of the condyle 6 and laterally delimited by a receptacle side face 52 which extends in a circular manner around the center axis 46.

The base plate 8 is in turn anchored to the Cavitas Glenoidalis 102 by means of the protrusions 18 and the anchoring screws 26, 28, 30. In this instance, it is particularly significant—as can be seen from the illustration of FIG. 15 in particular—for the base plate 8 to be arranged on the Cavitas Glenoidalis 102 in an offset state in the direction towards the Angulus Inferior. This prevents to the greatest possible extent abutment of the edge 106 of the articulation socket when the arm is abducted towards the upper body. Even when the upper arm is adducted to an extremely high degree, as illustrated in FIG. 16, it is not possible for the articulation socket edge 106 to abut the anchoring elements.

This desired offset arrangement of the base plate 8 is particularly promoted by the fact that the center 47 of the dome shape of the base face 22 of the base plate 8 is formed eccentrically relative to the center axis 45 of the base plate 8. In particular, this center 47 is displaced in the opposite direction to the Angulus Inferior 90 of the scapula 88. This particular configuration results in the surface of the Cavitas Glenoidalis 102 being able to have a spherical-portion-shaped recess which is particularly preferred for assembly of the shoulder prosthesis 2 since, owing to the offset arrangement, the center of the support region of the base face 22 now coincides with the center 47 of the dome shape. The processing of the Cavitas Glenoidalis 102 which is required prior to assembly of the shoulder prosthesis 2 is therefore relatively simple for a surgeon to carry out, uniform abutment of the base face 22 on the Cavitas Glenoidalis 102 over the entire contact face region nonetheless being achievable. It is significant for the shape of the base plate 8 to be adapted in an optimum manner to the specific bone conditions, whereby simple but also particularly reliable securing of the prosthesis 2 to the shoulder blade is enabled. This is a significant advantage compared with solutions according to the prior art in which the base face of the base plate was, for example, planar and the bone accordingly had to be highly processed and manipulated in order to allow the prosthesis to be secured.

The use of the two protrusions 18 on the base plate 8 according to the invention also further allows the use of an anchoring screw which is directed downwards to be dispensed with. Even if the arm—as illustrated in FIG. 16—is adducted to an extremely high degree and accordingly, over a period of time, wear of the bone material 88 of the shoulder blade occurs at the corresponding contact location, it is not possible at any time for the articulation socket edge 106 to collide with the protrusions 18 and/or one of the anchoring screws 26, 28, 30. The risk of one of the screws 26, 28, 30 becoming damaged over time and accordingly secure anchoring of the condyle 6 on the shoulder blade no longer being ensured is prevented in this manner.

The use of the two protrusions 18 also further allows the slightly more central arrangement of the two central anchoring screws 28, 30. Since the bone material of the shoulder blade is relatively thin at the Cavitas Glenoidalis 102, it is thus nonetheless ensured that the screws 28, 30 are securely introduced into the bone material and can penetrate therein over a sufficient length. Therefore, the anchoring of the condyle 6 is thereby again further improved.

Finally, the two protrusions 18 also allow the base plate 18 to be arranged on the previously processed Cavitas Glenoidalis 102 in the correct position in a manner which is secure in terms of rotation. Prior to the final assembly of the shoulder prosthesis 2, the corresponding holes for the protrusions 18 are generally marked using a template or positioning gauge, predrilled and then formed in the bone material. When a single protrusion 18 is used according to the previous solutions, it was not possible to exclude, during the subsequent assembly of the base plate 8, twisting thereof relative to the anterior/posterior and inferior/superior rotational orientation defined beforehand, which ultimately led to incorrect positioning or incorrect orientation of the screws and consequently the whole condyle 6. This resulted in the anchoring screws often protruding into regions in which there was no bone material. This problem does not occur when two protrusions 18 are used according to the invention since the two openings for the protrusions define a rotational orientation for the base plate 8 so that, with a relatively low level of complexity, it is possible to fix the shoulder prosthesis to the shoulder blade in a precise and secure manner.

The use of two protrusions on the base plate therefore also in principle affords advantages even when the base face does not have the eccentricity described above. Although this specific configuration affords additional advantages, the invention generally relates to inverse shoulder prostheses—for example, also to conventional configurations in which the base face of the base plate is constructed in a planar manner or in which the base face of the base plate is constructed in a dome-like manner, but without any eccentricity of the center point of the dome relative to the center axis of the base plate.

Figure 17:
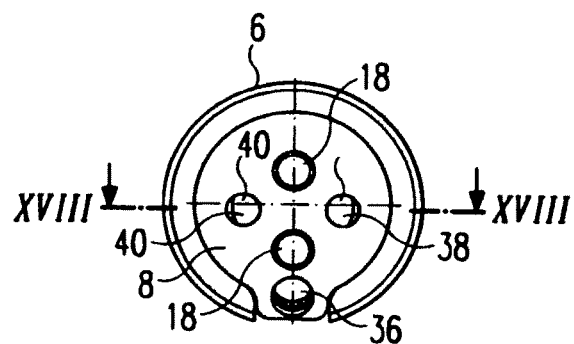
FIGS. 17 to 19 are views of an alternative configuration of a shoulder prosthesis according to the invention.
Figure 18:
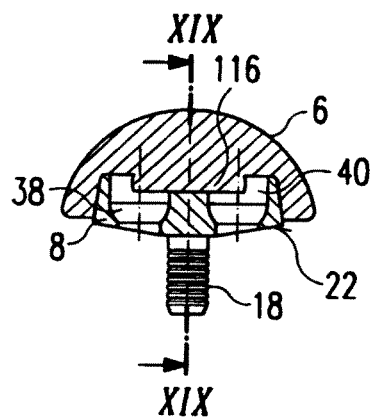
Figure 19:
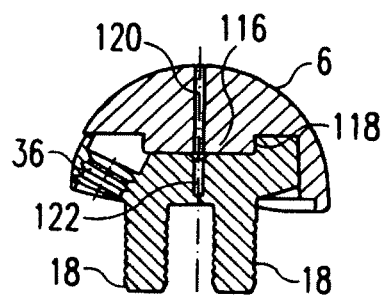

An alternative configuration for the base plate 8 and the condyle 6 is illustrated, for example, in FIGS. 17 to 19, elements of these two components which are identical to the components of the base plate 8 and condyle 6 described above being given the same reference numerals. Only the differences in this variant with respect to the first embodiment are to be referred to below.

The significant difference of this second variant involves the configuration of the contact region between the base plate 8 and the condyle 6. At the side of the base plate 8 facing the condyle 6, there is provided an indentation or circular recess 118 in which a corresponding cylinder-like protrusion 116 engages at the lower side of the condyle 6. The absorption of radial forces in the joined-together state is again improved by this engagement.

A further difference consists in that a central hole 120 extends through the condyle 6 and merges into a corresponding bore 122 in the base plate 8. The two bores 120, 122 can be used to receive a guiding or centering pin (not illustrated) which facilitates the arrangement of the condyle 6 on the base plate 8.

With regard to the additional configurations, the second variant corresponds to the first embodiment. Again, therefore, the base face 22 of the base plate 8 is constructed with two protrusions 18 and is provided with an eccentric dome-like shape. However, as already mentioned, the dome-shape could also be formed centrally or the base face 22 of the base plate 8 could even be planar.

In sum, the solution according to the invention therefore allows the condyle to be mounted on the shoulder blade in a manner which is not only simple to implement but which is also particularly reliable. Furthermore, the individual components of the shoulder prosthesis according to the invention are configured in such a manner that it is possible to prevent damage to the elements which are intended for anchoring on the shoulder blade, brought about in particular by inferior notching which can never be completely avoided.

The invention claimed is:

1. A shoulder prosthesis comprising:
an articulation socket and a condyle that co-operates with the articulation socket and with a scapula-side base plate in the manner of a clamping connection, the condyle being fitted to the base plate by a receptacle formed on the condyle and which can be anchored to a Cavitas Glenoidalis of a scapula by two pegs integrally formed with the base plate, wherein the base plate can be anchored to the Cavitas Glenoidalis by first or second anchoring screws received in first or second sleeves provided on the base plate, the first and second sleeves being symmetrically arranged about a straight connecting line between the two pegs, wherein a third sleeve is configured to guide a third anchoring screw in an angularly stable manner in which said third anchoring screw is laterally splayed toward an upper side of the base plate, and the third sleeve includes a screw thread that forms a screw connection between the base plate and said third anchoring screw, the prosthesis further comprising a groove on the condyle that co-operates with a tongue formed on the base plate, wherein the third sleeve is formed on the base plate in the region of the tongue.

2. A shoulder prosthesis according to claim 1, wherein the base plate can be secured on the Cavitas Glenoidalis in a direction offset toward an Angulus Inferior of the scapula.

3. A shoulder prosthesis according to claim 2, wherein the base plate has a dome-shaped base face provided for abutment against the Cavitas Glenoidalis of the scapula, a center of the dome-like shape being arranged eccentrically relative to a center axis of the base plate.

4. A shoulder prosthesis according to claim 3, wherein the center of the base face is arranged on the straight connecting line between the two pegs.

5. A shoulder prosthesis according to claim 3, wherein the center of the base face is displaced relative to the center axis of the base plate in a longitudinal direction toward the tongue formed in the base plate.

6. A shoulder prosthesis according to claim 1, wherein each sleeve, at a side of the base plate facing away from the scapula, has a recess for a head provided on the first or second anchoring screw.

7. A shoulder prosthesis according to claim 1, wherein the first and second sleeves are constructed such that the first and second anchoring screws associated with the first and second sleeves are oriented with a slight clearance substantially parallel with the pegs.

8. A shoulder prosthesis according to claim 1, wherein the receptacle of the condyle is formed centrally relative to a center axis thereof.

9. A shoulder prosthesis according to claim 1, wherein a receptacle side face on the condyle and an outer face of the base plate that co-operates therewith are constructed so as to be circular to form the clamping connection.

10. A shoulder prosthesis according to claim 1, wherein the pegs have ribs.

11. A shoulder prosthesis according to claim 1, wherein, in continuation of the receptacle provided on the condyle on the base plate, a bore is formed in the region of one of the two pegs with a centering pin extending into both the receptacle and the bore.

12. A shoulder prosthesis according to claim 1, wherein an outer face of the condyle comprises a lip extending from a side opposite of the groove in the condyle.

13. A shoulder prosthesis according to claim 1, wherein each of the first, second and third sleeves includes an unthreaded recess for receiving a screw head of the first, second or third anchoring screw.

14. A shoulder prosthesis according to claim 13, wherein the screw thread of the third sleeve is disposed between the unthreaded recess of the third sleeve and a base face of the base plate.

* * * * *